(12) United States Patent  
Michaels

(10) Patent No.: US 8,025,173 B2
(45) Date of Patent: Sep. 27, 2011

(54) COLLAPSIBLE CANISTER LINER FOR MEDICAL FLUID COLLECTION

(75) Inventor: Thomas L. Michaels, McCullom Lake, IL (US)

(73) Assignee: Allegiance Corporation, McGaw Park, IL (US)

( * ) Notice: Subject to any disclaimer, the term of this patent is extended or adjusted under 35 U.S.C. 154(b) by 479 days.

(21) Appl. No.: 11/517,125

(22) Filed: Sep. 7, 2006

(65) Prior Publication Data

US 2008/0061064 A1   Mar. 13, 2008

(51) Int. Cl.
*B65D 25/14* (2006.01)
*B65D 35/14* (2006.01)
*B65D 90/00* (2006.01)

(52) U.S. Cl. ............... 220/495.06; 220/495.08

(58) Field of Classification Search ............ 220/9.2, 220/495.08, 666, 495.06; 383/33, 104, 119; 215/11.3
See application file for complete search history.

(56) References Cited

U.S. PATENT DOCUMENTS

| | | | | |
|---|---|---|---|---|
| 687,790 A * | 12/1901 | Scales | | 222/92 |
| 2,057,238 A | 10/1936 | Krug | | |
| 2,686,625 A | 8/1954 | Sundholm | | |
| 3,035,623 A * | 5/1962 | Goetz | | 220/675 |
| 3,164,186 A | 1/1965 | Weber et al. | | |
| 3,307,746 A | 3/1967 | Edwards | | |
| 3,515,127 A | 6/1970 | Reymond | | 128/2 |
| 3,773,211 A | 11/1973 | Bridgman | | |
| 3,780,738 A * | 12/1973 | Deaton | | 604/540 |
| 3,814,098 A | 6/1974 | Deaton | | |
| 3,830,238 A | 8/1974 | Kurtz et al. | | 128/275 |
| 3,915,189 A | 10/1975 | Holbrook et al. | | |
| 3,924,772 A | 12/1975 | Magnani | | |
| 4,022,258 A | 5/1977 | Steidley | | |
| 4,173,295 A | 11/1979 | Steinman | | |
| 4,346,711 A | 8/1982 | Agdanowski et al. | | 128/276 |
| 4,379,455 A | 4/1983 | Deaton | | |
| 4,392,860 A | 7/1983 | Huck et al. | | |
| 4,397,643 A | 8/1983 | Rygiel | | 604/317 |
| 4,419,093 A * | 12/1983 | Deaton | | 604/540 |
| 4,455,140 A | 6/1984 | Joslin | | 604/317 |
| 4,460,361 A | 7/1984 | Nichols | | |
| 4,492,313 A | 1/1985 | Touzanit | | 215/1 |
| 4,515,283 A | 5/1985 | Suzuki | | |
| 4,541,457 A | 9/1985 | Blenkush | | |
| 4,568,006 A | 2/1986 | Mueller et al. | | |

(Continued)

FOREIGN PATENT DOCUMENTS

WO   WO 80/01558   8/1980

OTHER PUBLICATIONS

International Search Report dated Jul. 30, 2008, 13 pages.

(Continued)

*Primary Examiner* — Harry Grosso
(74) *Attorney, Agent, or Firm* — Arent Fox LLP

(57) ABSTRACT

A collapsible liner for use in a canister of a medical fluid collection system is disclosed. The liner includes a flexible bag extending longitudinally between a top portion opposite a closed bottom portion, and at least one support element connected to the bag and disposed generally laterally relative to a length of the bag. When an interior of the bag is subjected to a vacuum, the at least one support element limits an extent of lateral collapse while permitting longitudinal collapse.

20 Claims, 9 Drawing Sheets

U.S. PATENT DOCUMENTS

| | | |
|---|---|---|
| 4,569,674 A | 2/1986 | Phillips et al. |
| 4,642,128 A | 2/1987 | Solorzano |
| 4,650,477 A | 3/1987 | Johnson |
| 4,769,019 A | 9/1988 | Kerwin |
| 4,775,366 A | 10/1988 | Rosenblatt ............. 604/181 |
| 4,790,453 A | 12/1988 | Fontana et al. |
| 4,799,924 A | 1/1989 | Rosenblatt ............. 604/181 |
| 4,799,925 A | 1/1989 | Rosenblatt ............. 604/181 |
| 4,863,446 A | 9/1989 | Parker |
| 4,874,023 A | 10/1989 | Ulm |
| 4,906,261 A | 3/1990 | Mohajer |
| 4,921,679 A | 5/1990 | Martin et al. |
| 4,925,447 A | 5/1990 | Rosenblatt ............. 604/133 |
| 4,930,997 A | 6/1990 | Bennett |
| 4,948,010 A | 8/1990 | Wiggins |
| 4,950,247 A | 8/1990 | Rosenblatt ............. 604/181 |
| 4,957,491 A | 9/1990 | Parker |
| 4,957,492 A | 9/1990 | McVay |
| 4,963,134 A | 10/1990 | Backscheider et al. |
| 4,976,694 A | 12/1990 | Schreibman |
| 4,979,628 A * | 12/1990 | Robbins, III ............. 215/395 |
| 4,981,473 A * | 1/1991 | Rosenblatt ............. 604/133 |
| 4,986,839 A | 1/1991 | Wertz et al. |
| 5,002,534 A | 3/1991 | Rosenblatt ............. 604/133 |
| 5,010,179 A | 4/1991 | Lai |
| 5,027,963 A * | 7/1991 | Robbins, III ............. 215/395 |
| 5,039,494 A | 8/1991 | Martin et al. |
| 5,072,762 A | 12/1991 | Jimenez |
| 5,084,250 A | 1/1992 | Hall |
| 5,124,126 A | 6/1992 | Ripp |
| 5,156,602 A | 10/1992 | Steffler |
| 5,178,828 A | 1/1993 | Uesugi |
| 5,185,007 A | 2/1993 | Middaugh et al. |
| 5,209,565 A | 5/1993 | Goncalves |
| 5,217,038 A | 6/1993 | Pinder |
| 5,217,688 A | 6/1993 | Von Lersner |
| 5,234,419 A | 8/1993 | Bryant et al. |
| 5,242,434 A | 9/1993 | Terry |
| 5,242,474 A | 9/1993 | Herbst et al. |
| 5,252,290 A | 10/1993 | Uesugi |
| 5,269,030 A | 12/1993 | Pahno et al. |
| 5,279,602 A | 1/1994 | Middaugh et al. |
| 5,295,518 A | 3/1994 | Baker et al. |
| 5,309,924 A | 5/1994 | Peabody ............. 128/765 |
| 5,318,516 A | 6/1994 | Cosmescu |
| 5,333,761 A * | 8/1994 | Davis et al. ............. 222/212 |
| 5,370,270 A | 12/1994 | Adams et al. |
| 5,380,289 A | 1/1995 | Hemstreet et al. |
| 5,417,655 A | 5/1995 | Divilio et al. |
| 5,423,779 A | 6/1995 | Yeh |
| 5,438,721 A | 8/1995 | Pahno et al. |
| 5,470,324 A | 11/1995 | Cook et al. |
| 5,494,074 A | 2/1996 | Ramacier, Jr. et al. |
| 5,514,119 A | 5/1996 | Curtis |
| 5,520,668 A | 5/1996 | Greff et al. |
| 5,522,808 A | 6/1996 | Skalla |
| 5,549,585 A | 8/1996 | Maher et al. |
| 5,588,167 A | 12/1996 | Pahno et al. |
| 5,607,411 A | 3/1997 | Heironimus et al. |
| 5,620,428 A | 4/1997 | Hand |
| 5,637,103 A | 6/1997 | Kerwin et al. |
| 5,645,540 A | 7/1997 | Henniges et al. |
| 5,653,270 A | 8/1997 | Burrows |
| 5,669,892 A | 9/1997 | Keogh et al. |
| 5,683,371 A | 11/1997 | Hand |
| 5,685,835 A | 11/1997 | Brugger |
| 5,688,255 A | 11/1997 | Hand |
| 5,720,078 A | 2/1998 | Heintz |
| 5,741,237 A | 4/1998 | Walker |
| 5,741,238 A | 4/1998 | Bradbury et al. |
| 5,776,118 A | 7/1998 | Seifert et al. |
| 5,776,260 A | 7/1998 | Dunn et al. |
| 5,785,044 A | 7/1998 | Meador et al. |
| 5,792,126 A | 8/1998 | Tribastone et al. |
| 5,797,506 A | 8/1998 | Lehmkuhl et al. |
| 5,807,230 A | 9/1998 | Argenta et al. |
| 5,807,359 A | 9/1998 | Bemis et al. |
| 5,830,198 A | 11/1998 | Henniges et al. |
| 5,836,909 A | 11/1998 | Cosmescu |
| 5,855,289 A | 1/1999 | Moore |
| 5,871,476 A | 2/1999 | Hand |
| 5,885,240 A | 3/1999 | Bradbury et al. |
| 5,901,717 A | 5/1999 | Dunn et al. |
| 5,910,291 A | 6/1999 | Skalla et al. |
| 5,914,047 A | 6/1999 | Griffiths |
| 5,931,822 A | 8/1999 | Bemis et al. |
| 5,944,703 A | 8/1999 | Dixon et al. |
| 5,945,004 A | 8/1999 | Ohira et al. |
| 5,947,171 A | 9/1999 | Woodruff |
| 5,968,032 A | 10/1999 | Sleister |
| 5,975,096 A | 11/1999 | Dunn et al. |
| 5,985,009 A | 11/1999 | Marsala |
| 5,997,733 A | 12/1999 | Wilbur et al. |
| 6,017,493 A | 1/2000 | Cambron et al. |
| 6,024,124 A | 2/2000 | Braun et al. |
| 6,027,490 A | 2/2000 | Radford et al. |
| 6,039,724 A | 3/2000 | Seifert et al. |
| 6,045,596 A | 4/2000 | Holland, Jr. et al. |
| 6,056,731 A * | 5/2000 | Koetke et al. ............. 604/323 |
| 6,082,401 A | 7/2000 | Braun et al. |
| 6,105,638 A | 8/2000 | Edwards et al. |
| 6,152,902 A | 11/2000 | Christian et al. |
| 6,161,578 A | 12/2000 | Braun et al. |
| 6,180,000 B1 | 1/2001 | Wilbur et al. |
| 6,203,590 B1 | 3/2001 | Byrd et al. |
| 6,231,089 B1 | 5/2001 | Decler et al. |
| 6,244,311 B1 | 6/2001 | Hand et al. |
| 6,258,232 B1 | 7/2001 | Hasegawa et al. |
| 6,261,276 B1 | 7/2001 | Reitsma |
| 6,263,887 B1 | 7/2001 | Dunn |
| 6,280,867 B1 | 8/2001 | Elias |
| 6,331,246 B1 | 12/2001 | Beckham et al. |
| 6,358,232 B1 | 3/2002 | Hand et al. |
| 6,368,310 B1 | 4/2002 | Bemis et al. |
| 6,488,675 B1 | 12/2002 | Radford et al. |
| 6,494,391 B2 | 12/2002 | Mosenson et al. |
| 6,494,869 B1 | 12/2002 | Hand et al. |
| 6,499,495 B2 | 12/2002 | Jeng |
| 6,524,307 B1 | 2/2003 | Palmerton et al. |
| 6,588,436 B2 | 7/2003 | Dunn et al. |
| 6,626,877 B2 | 9/2003 | Anderson et al. |
| 6,652,495 B1 | 11/2003 | Walker |
| 6,672,477 B2 | 1/2004 | Miller et al. |
| 6,673,055 B2 | 1/2004 | Bemis et al. |
| 6,676,644 B2 | 1/2004 | Ikeda |
| 6,705,591 B2 | 3/2004 | Decler |
| 6,755,807 B2 | 6/2004 | Risk, Jr. et al. |
| 6,770,061 B2 | 8/2004 | Wildman |
| 6,776,175 B2 | 8/2004 | Dunn et al. |
| 6,800,074 B2 | 10/2004 | Henley et al. |
| 6,824,533 B2 | 11/2004 | Risk, Jr. et al. |
| 6,893,425 B2 | 5/2005 | Dunn et al. |
| 6,902,673 B2 | 6/2005 | Smit et al. |
| 6,976,977 B2 | 12/2005 | Yam |
| 7,090,663 B2 | 8/2006 | Dunn et al. |
| 7,115,115 B2 | 10/2006 | Bemis et al. |
| 7,163,618 B2 | 1/2007 | Beckham et al. |
| 7,258,711 B2 | 8/2007 | Dunn et al. |
| 7,328,816 B2 | 2/2008 | Shannon et al. |
| 7,469,727 B2 | 12/2008 | Marshall |
| 7,497,340 B2 | 3/2009 | Hershberger et al. |
| 2004/0102743 A1 | 5/2004 | Walker |
| 2004/0164076 A1 | 8/2004 | Baker et al. |
| 2004/0204693 A1 | 10/2004 | Anderson et al. |
| 2005/0069696 A1 | 3/2005 | King et al. |
| 2005/0139532 A1 | 6/2005 | Hershberger et al. |
| 2005/0171495 A1 | 8/2005 | Austin et al. |
| 2005/0187528 A1 | 8/2005 | Berg |
| 2005/0187529 A1 | 8/2005 | Reasoner et al. |
| 2005/0189283 A1 | 9/2005 | Smit et al. |
| 2007/0135778 A1 | 6/2007 | Murray et al. |
| 2007/0135779 A1 | 6/2007 | Lalomia et al. |
| 2008/0053539 A1 | 3/2008 | Hershberger et al. |
| 2009/0005747 A1 | 1/2009 | Michaels et al. |
| 2009/0012485 A1 | 1/2009 | Michaels et al. |
| 2009/0159535 A1 | 6/2009 | Hershberger et al. |

OTHER PUBLICATIONS

International Search Report Dated Jun. 20, 2008 11 pages.
Figures, Neptune 2 Ultra, Waste Management System, 2 pages; as viewed at http://www.stryker.com/stellent/groups/instruments/documents/web_prod/059445.pdf, Feb. 21, 2008, pp. 1-2.

* cited by examiner

COLLAPSIBLE CANISTER LINER FOR MEDICAL FLUID COLLECTION

BACKGROUND

The present invention relates to canister liners for use in medical fluid collection systems. More particularly, it relates to devices, systems, and methods for controlling longitudinal and lateral collapse of a liner bag within a canister during evacuation of medical fluids from the liner bag.

Hospitals and clinics routinely collect a significant volume of medical waste fluids. The medical waste fluids are collected from a variety of sites, including patient operative and post-operative sites, and various other locations within the hospitals and clinics. After the medical waste fluid is collected, there is a desire to dispose of the waste in a manner that protects healthcare workers and others from contact with the waste fluids, complies with hospital and other guidelines, and is cost effective.

Hospitals and clinics dispose of collected medical waste fluids in a variety of ways. For example, some medical waste is suited for disposal down a drain connected to a city sewer system. Some liquid medical waste is first solidified and then disposed of in a solid waste stream. For example, the addition of super absorbent polymers (as commonly used in infant diapers to solidify liquid waste) to medical waste liquids forms a solid gel that is more convenient to handle when disposing of the waste.

Other medical waste is collected in a rigid container and hauled away from the hospital or clinic by a contractor, usually for disposal in a landfill. Yet another method of disposing of collected medical waste includes safely pumping the collected medical waste from a canister system down a drain or other reservoir suitable for subsequent treatment and/or disposal. For example, one such suitable canister system is a Medi-Vac® Flex Advantage® suction canister available from Cardinal Health, Dublin, Ohio. This canister system includes a liner bag inside a rigid canister. Medical waste is collected in the liner bag and subsequently disposed of by having a worker insert a dip tube into the liner bag and safely pump the medical waste through the dip tube and out the liner bag. In this regard, the insertion of the dip tube into and out of the liner bag can be inconvenient to the worker. In addition, even after the medical waste is evacuated from the liner bag, these conventional liner bags can still be undesirably large and bulky. Some facilities require the worker to manually collapse the emptied liner bag before discarding it, which is time consuming and may be somewhat unpleasant for the worker.

All of the above-noted methods for collecting and disposing of medical waste require the eventual disposal of some sort of bulk material, whether in the form of a solidified gel or a used container or liner. Generally, the greater the amount of bulk material that is disposed of, the greater the ultimate economic cost for disposal, and this cost is borne by the hospital or clinic. In addition, the disposal of unnecessarily bulky material (i.e., material that occupies more landfill space) is environmentally undesirable. With this in mind, improvements in devices and systems that collect and enable the safe disposal of medical waste fluids will be enthusiastically welcomed by hospitals and clinics.

SUMMARY

Benefits achieved in accordance with principles of the disclosed invention include a collapsible liner that collapses along its longitudinal axis to minimize a volume of the collapsed liner, which minimizes a volume of material that is ultimately disposed of by an end user. This compact, reduced volume liner contributes to ease of handling by users (e.g., hospital staff) and also to reduced disposal volume. Other benefits include a collapsible liner that can be evacuated without using a dip tube. Still other benefits include a simultaneous and controlled longitudinal and lateral collapse of the collapsible liner during evacuation that prevents the potential undesired trapping of waste fluids in un-collapsed pockets of the liner.

Some aspects of the present invention relate to a collapsible liner for use in a canister of a medical fluid collection system. The liner includes a flexible bag extending longitudinally between a top portion opposite a closed bottom portion, and at least one support element connected to the bag and disposed generally laterally relative to a length of the bag. In this regard, when an interior of the bag is subjected to a vacuum, the support element(s) limits an extent of lateral collapse of the bag while permitting a longitudinal collapse.

Other aspects of the present invention relate to a liner assembly for use with a medical fluid collection canister. The liner assembly includes a lid that is removably attachable to the canister and a liner coupled to the lid. The liner includes a flexible film bag extending longitudinally between a top portion and a closed bottom portion, and at least one support element apart from the lid and connected to a segment of the bag. In this regard, when an interior of the bag is subjected to a vacuum, the bag longitudinally collapses and the segment(s) of the bag coupled to the support element(s) do not laterally collapse.

Still other aspects of the present invention relate to a medical fluid collection system. The system includes a canister defining an open end and a liner assembly. The liner assembly includes a lid removably attachable to the open end of the canister, and a collapsible liner dimensioned for placement within the canister. In this regard, the liner includes a flexible film bag extending longitudinally between a top portion coupled to the lid and a closed bottom portion, and at least one support element disposed generally laterally relative to the flexible bag. When an interior of the bag is subjected to a vacuum, the support element constrains a lateral collapse of the bag.

BRIEF DESCRIPTION OF THE DRAWINGS

The accompanying drawings are included to provide a further understanding of the present invention and are incorporated in and are a part of this specification. Other embodiments of the present invention, and many of the intended advantages of the present invention, will be readily appreciated as they become better understood by reference to the following detailed description. The elements of the drawings are not necessarily to scale relative to each other. Like reference numerals designate corresponding similar parts.

DETAILED DESCRIPTION

Figure 1:
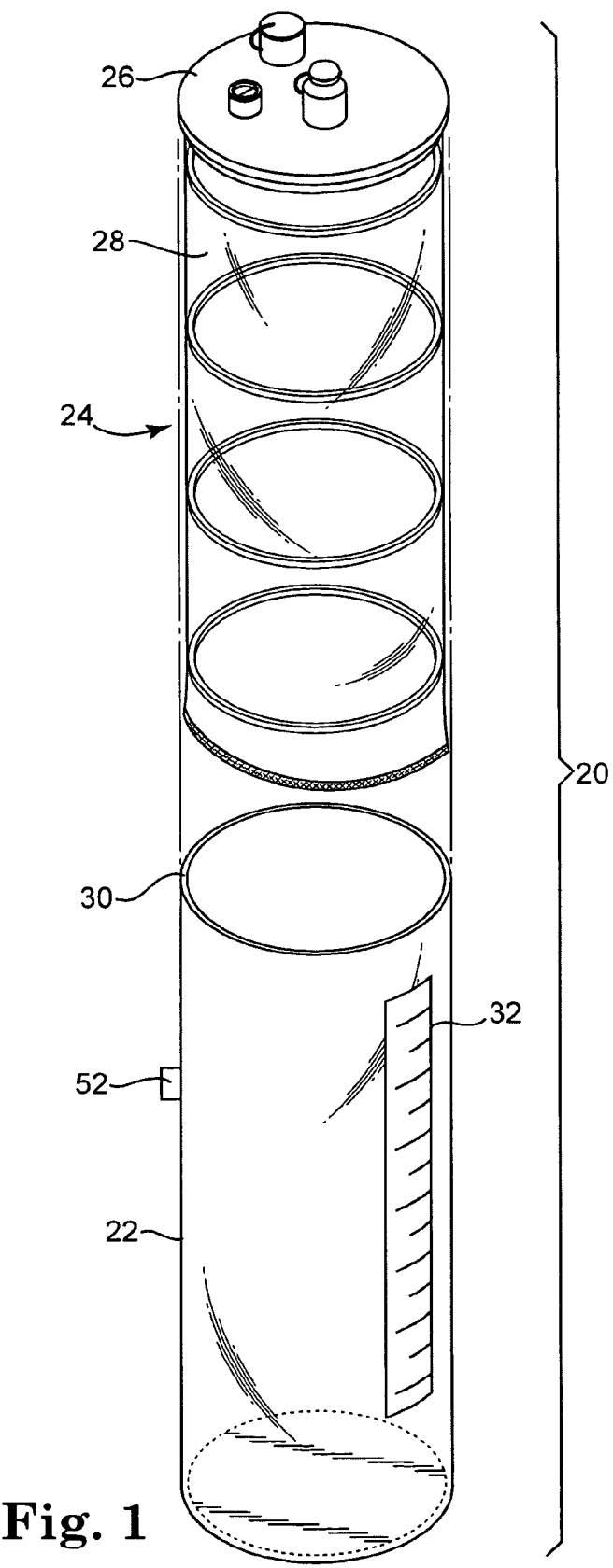
FIG. 1 illustrates a perspective exploded view of components of a medical fluid collection system in accordance with principles of the present invention.

FIG. 1 illustrates a perspective exploded view of components of a medical fluid collection system 20 according to principles of the present invention. The system 20 includes a canister 22 and a liner assembly 24 removably coupleable to the canister 22. The liner assembly 24 includes a lid 26 and a collapsible liner 28 coupled to the lid 26. Details of the various components of the system 20 are provided below. In general terms, however, the lid 26 of the liner assembly 24 is sized to be attached and sealed to an open end 30 defined by the canister 22, and the collapsible liner 28 is sized to be disposed within the canister 22. The collapsible liner 28 is a repository for the collection of medical waste fluids, and is configured to uniformly and compactly collapse to expel the contained medical waste fluids (not shown) during a disposal process.

The canister 22 is generally a durable, impact resistant molded container. In some embodiments, the canister 22 is reusable and suited for repeated use with single use, disposable liner assemblies 24. The canister 22 illustrated is a cylindrical canister, although other shapes and sizes of canister 22 are also acceptable. In one embodiment, the canister 22 is sized to receive the collapsible liner 28 otherwise having a collection volume that ranges between about 1 liter to 20 liters. The canister 22 can be molded from high impact plastic, and in some embodiments includes a graduated scale 32 useful in measuring a collected volume of medical waste. Suitable rigid canisters 22 include canisters provided as a component of a Medi-Vac® Suction Canister System, available from Cardinal Heath of Dublin, Ohio.

Figure 2:
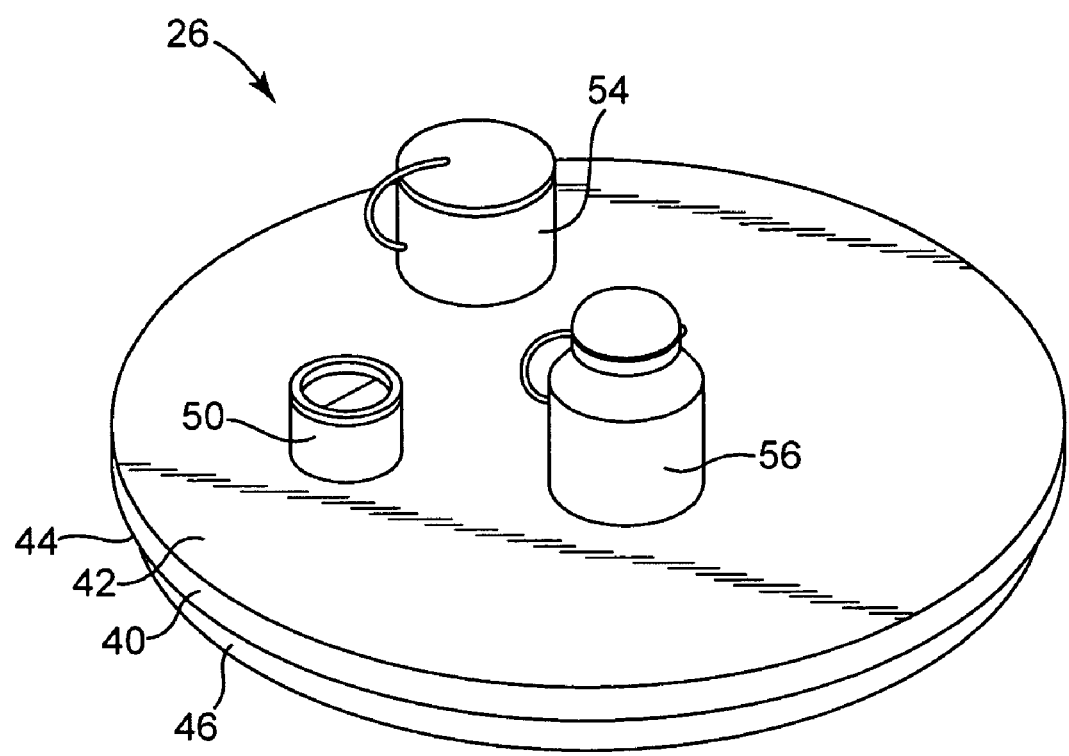
FIG. 2 is a perspective view of a lid component of a liner assembly of the system of FIG. 1.

FIG. 2 illustrates a perspective view of one embodiment of the lid 26. The lid 26 includes a rim 40 extending between an upper surface 42 and a lower surface 44, and a flange 46 that extends from the lower surface 44. The flange 46 can be sized to receive an open end of the collapsible liner 28 (FIG. 1). Alternatively, other configurations that promote assembly of the collapsible liner 28 are also acceptable; for example, the liner 28 can be assembled (e.g., bonded) to an underside of the lid 28 or at some other surface that may or may not be cylindrical.

In general, the lid 26 is provided as one component of the liner assembly 24 (FIG. 1), and can include one or more ports useful in the collection and subsequent discharge of medical fluids. For example, in some embodiments the lid 26 includes a first vacuum source port 50, a discharge port 54, and a collection port 56. Although three ports are illustrated, it is to be understood that fewer than three ports, or more than three ports, are also acceptable configurations for the lid 26.

The first vacuum source port 50 is sized for coupling to a vacuum line (not shown) and facilitate partial evacuation of the collapsible liner 28 for the purpose of collecting medical waste fluid within the liner 28. More particularly, upon assembly of the lid 22/liner 28, the first vacuum source port 50 is fluidly connected with an interior of the liner 28, such that application of a vacuum to the port 50 renders the liner interior below atmospheric pressure. Conversely, waste fluid to be collected (e.g., via the patient tubing port 56 as described below) is at atmospheric pressure. Thus, the below atmospheric pressure condition causes the medical waste fluid to flow into the liner 28. With this in mind, in some embodiments, the first vacuum source port 50 can include an internal vacuum shutoff valve (not shown) configured to interrupt the vacuum source when the liner 28 is nearly filled with medical waste fluid and thereby prevent the passage of medical waste fluid through the first vacuum source port 50 and into the vacuum line. In further embodiments, the first vacuum source port 50 is configured to receive and maintain a shutoff device (no shown), such as a cap or valve, for use when fluid within the liner 28 is disposed of as described below.

With additional reference to FIG. 1, fluid collection via application of a vacuum at the first vacuum source port 50 as described above can be further enhanced, in some embodiments, by a second vacuum source port 52. The second vacuum source port 52 is sized for coupling to a vacuum line (not shown) and facilitates partial evacuation of a space between the collapsible liner 28 and the canister 22. More particularly, a vacuum is applied, via the second vacuum source port 52, to the space between the collapsible liner 28 and the canister 22 commensurate with the vacuum applied to the liner 28 interior (via the first vacuum source port 50 as described above). With this approach, then, the collapsible liner 28 will not collapse as medical waste fluid is drawn into, and collected within, the liner 28. In some embodiments, the second vacuum source port 52 includes a three-way valve (not shown) that fluidly connects the space between the liner 28 and the canister 22 with a vacuum source in one position and atmospheric air in a second position, although other configurations are also acceptable. While the second vacuum source port 52 is shown as being formed as part of the canister 22, in other embodiments, the second vacuum source port 52 can be provided with the lid 26. Even further, the system 20 can be configured in other embodiments to facilitate medical waste fluid collection within the liner 28 in a manner that does not require one or both of the vacuum source ports 50 and/or 52.

The discharge port 54 is sized to receive a vacuum line (not shown) for evacuating medical waste fluid from the collapsible liner 28 (FIG. 1) during a waste disposal procedure, described in FIGS. 8A and 8B below. In this regard, the discharge port 54 is closed during collection of medical waste fluid into the liner 28, and thus can include a closure device (not shown) such as a valve, cap, etc.

The collection port 56 is configured for connection to collection tubing (not shown). The collection tubing removes or otherwise aspirates away from a collection site (e.g., a patient) waste liquids or other medical fluids through the collection port 56 via the below atmospheric pressure created within the liner 28 as described above. In some embodiments, the collection port 56 is provided with a one-way valve (not shown) integrally formed within the port 56. The one-way valve prevents back flow of medical fluids from the system 20 back to the collection site. Alternatively, other configurations that may or may not include a valve are also acceptable. Regardless, upon final assembly, the collection port 56 is in fluid communication with the collapsible liner 28 and defines an entrance into the collapsible liner 28 for medical waste fluids.

Figure 3:
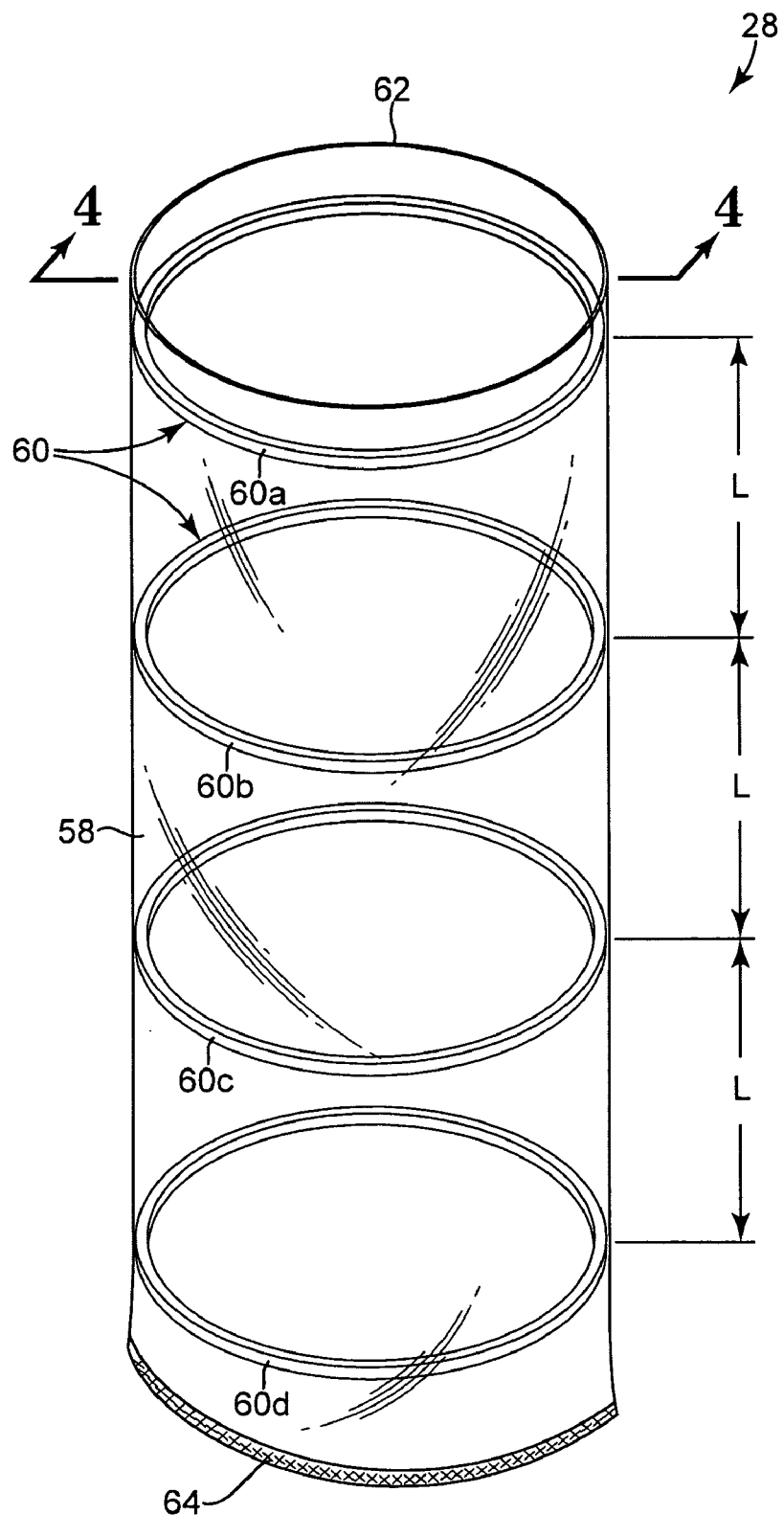
FIG. 3 is a perspective view of a collapsible liner component of a liner assembly of the system of FIG. 1.

FIG. 3 illustrates a perspective view of the collapsible liner 28 separate from the lid 26 (FIG. 2). The collapsible liner 28 includes a bag 58 and one or more support elements 60 disposed generally laterally relative to the bag 58. In the illustrated embodiment, the liner 28 includes four exemplary support elements 60a, 60b, 60c, 60d, although it is to be understood that the number of support elements 60 can vary depending upon the design goals for the liner 28.

In one embodiment, the bag 58 extends longitudinally between a top portion 62 that is opposite a closed bottom portion 64 to define an interior within which medical waste fluid (not shown) is contained. In general, the bag 58 is formed separately and attached to a lid, such as the lid 26 (FIG. 2). In this regard, the top portion 62 is coupled to the lid 26. The bag 58 is formed by suitable film forming processes including, for example, blown film processes, film extrusion processes in general, or other suitable thin plastic bag forming processes.

The bottom portion 64 is generally sealed, or otherwise closed off, to prevent the passage of fluids through the bottom portion 64 of the bag 58. In one embodiment, multiple bags 58 are continuously formed on a blown film extrusion line and the bottom portion 64 of a first bag 58 is heat sealed shut across its width as the top portion 62 of a second bag 58 is simultaneously cut and opened across its width. Other suitable processes for forming the bag 58 and sealing the bottom portion 64 are also acceptable.

Generally, the bag 58 is formed of a thin, flexible material. For example, in some embodiments, the bag 58 material exhibits sufficient flexibility to longitudinally and laterally collapse in the presence of 0.1-1 atmosphere (ATM) vacuum (as typically employed during a disposal operation). Suitable materials for the bag 58 include polyolefins in general, and polyethylene, low density polyethylene, linear low density polyethylene, high density polyethylene, polypropylene, and co-polymers and block co-polymers of polyolefins in particular. One suitable material for the bag 58 includes radio frequency (RF) weldable polymers, such as ethylene methyl acrylate, for example, which is a co-polymer of polyethylene. Other RF weldable polymers are also acceptable.

The support elements 60a, 60b, 60c, and 60d are provided to limit or constrain lateral collapse of the liner 28, and in particular the bag 58, when a vacuum is placed upon the bag interior. That is to say, the liner 28 collapses both laterally and longitudinally, but the lateral collapse is controlled to permit an essentially complete longitudinal collapse of the bag 58 from the bottom portion 64 up to the top portion 62 during evacuation of medical waste fluids (it being understood that the bag 58 will not, in some embodiments, experience a complete longitudinal collapse due to a height of the support element(s) 60). To this end, the support elements 60 are not flexible relative to a flexibility of the flexible bag 58, such that the support elements 60 are resistant to lateral (e.g., radial) collapse as the bag 58 is evacuated/collapsed. For example, a transverse rigidity of the support elements 60 (e.g., resistance to deflection or collapse in response to a transversely-applied compressive force) is at least five times greater; alternatively at least ten times greater; alternatively at least fifty times greater, than that of the bag 58. With this in mind, although four support elements 60a, 60b, 60c, 60d are illustrated, it is to be understood that one or more support elements can be generally laterally disposed relative to the bag 58 to control the lateral collapse of the bag 58, depending upon a ratio of height-to-width of the bag 58. In some embodiments, the support element(s) 60 is/are sealed to the bag 58. In other embodiments, the support element(s) 60 is/are integrally formed with the bag 58 during fabrication of the liner 28.

The support elements 60 are, in general, disposed generally laterally between the top portion 62 and the bottom portion 64 of the bag 58. For example, relative to the longitudinal cross-sectional view of FIG. 4, the flexible film bag 58 can be described as defining opposing faces 68, 70 that are separated by a lateral bag width W. Each of the support elements 60 are connected to the bag 58 so as to extend or be oriented generally laterally relative to a longitudinal length or axis of the bag 58 (e.g., each support element 60 is oriented or extends in a plane that is within 15° of a true perpendicular relationship with the longitudinal length or axis of the bag 58; in other embodiments, within 10°; and in other embodiments within 5°). Further, the support elements 60 are discretely distributed or positioned longitudinally between the top portion 62 and the closed bottom portion 64. In this regard, a longitudinal spacing L between adjacent ones of the support elements 60 is, in some embodiments, substantially uniform (±10%).

In some embodiments, the bag 58 is substantially circular in lateral cross-section such that the lateral bag width W is equal to a diameter of the bag 58. In other embodiments, the bag 58 is non-circular in lateral cross-section. In any regard, the spacing distance L between at least one pair of two adjacent support elements 60a, 60b, 60c, 60d (and in some embodiments between all adjacent pairs) is not greater than a minimum value of the lateral bag width W.

With this in mind, to minimize the size and cost of the lid to which the liner 28 is assembled (e.g., the lid 26 of FIG. 2) and particularly with certain high capacity liners 28 that contain up to, for example, 20 liters of liquid, a total length of the bag 58 can be substantially larger than the width W, and multiple support elements 60 are connected to the bag 58 and spaced the spacing distance L apart. Conversely, with liners 28 having a total length less than approximately two times the width W (e.g., typical for low volume liners 28), one support element 60 located between the top portion 62 and the closed bottom portion 64 of the bag 58 can be sufficient to limit or constrain the lateral collapse of the bag 58 (when subjected to a vacuum) to an amount or extent sufficient to prevent the bag 58 from laterally collapsing onto itself.

The support elements 60 are, in some embodiments, rigid annular plastic bands or rings that are suited for coupling to the bag 58. Generally, the support elements 60 resist radial/lateral deformation for lateral forces that correspond to about 1 ATM of vacuum within the liner 28. Suitable materials for forming the support elements 60 include polyolefins in general, such as high density polyethylene, and polyolefins that have a radiofrequency (RF) weldable component. In one embodiment, the support elements 60 are formed of a co-polymer of polyethylene, such as ethylene methyl acrylate, and are radiofrequency welded to the bag 58. Other suitable materials for forming the support elements 60 are also acceptable.

In various embodiments, the bag 58 is formed of a flexible film and the relatively rigid support elements 60 are RF welded or assembled or otherwise attached to the bag 58. In alternate embodiments, the liner 28 (including the bag 58 and the support elements 60) is integrally formed, for example by a molding process, such that the bag 58 is flexible in comparison to the more rigid support elements 60. For example, the bag 58 and the support elements 60 can be formed of similar materials where a caliper thickness of a wall of the bag 58 between the support elements 60 is relatively thin in comparison to a greater caliper thickness of the laterally spaced support elements 60. The integrally formed liner 28 can be fabricated in a batch molding process, for example, or preferably in a continuous blow molding process that includes forming the support elements 60 as lateral variations in film thickness.

Figure 4:
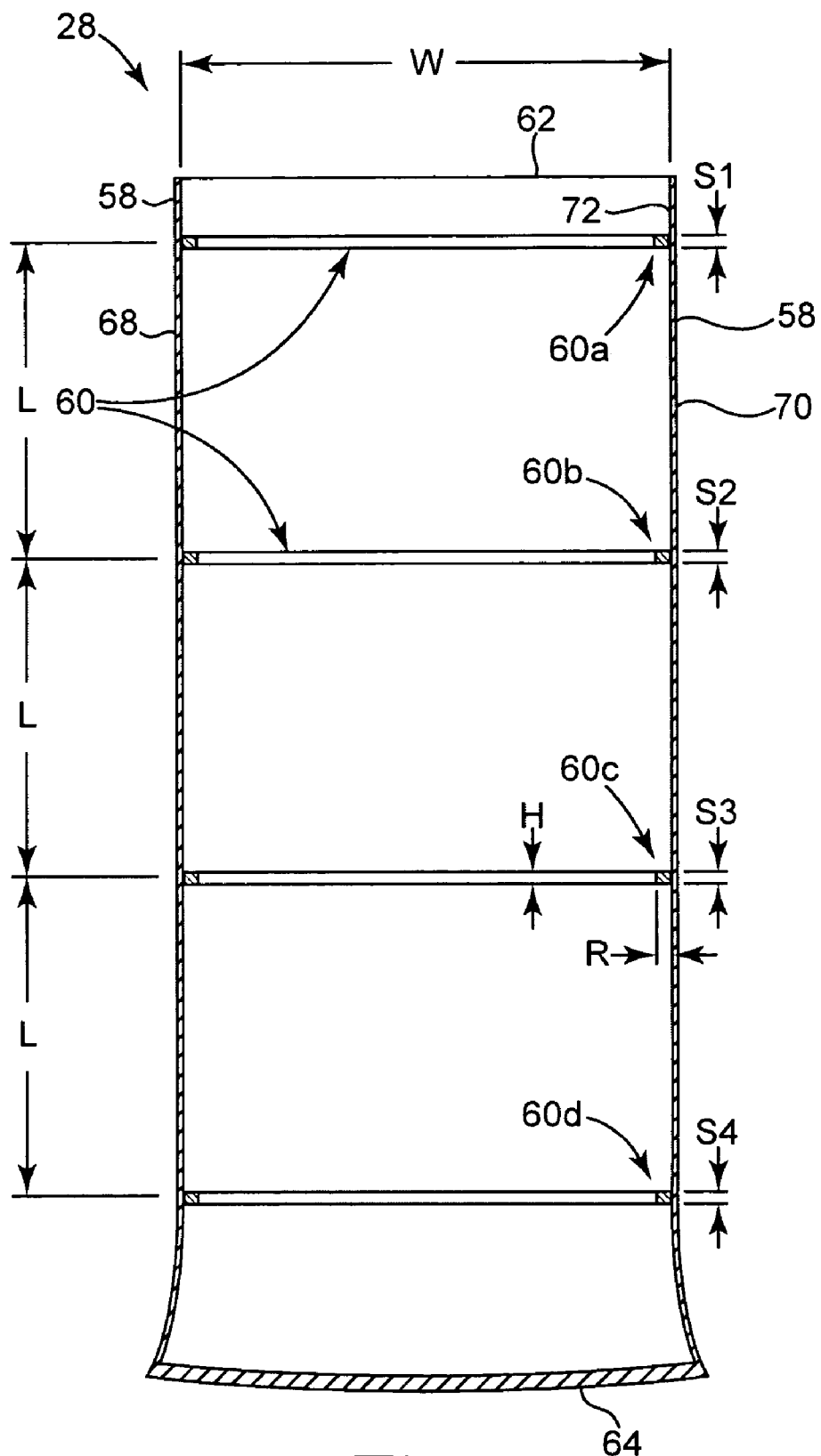
FIG. 4 is a cross-sectional view of the collapsible liner of FIG. 3.

In some embodiments, the support elements 60a, 60b, 60c, 60d are coupled to a respective segment S1, S2, S3, S4 of an interior surface 72 of the flexible film bag 58, as illustrated in FIG. 4. In alternative embodiments, the support elements 60 are coupled to an exterior surface of the flexible film bag 58.

In general, the support elements 60 have a similar configuration. In this regard, since the support elements 60a-60d are highly similar, a full understanding of the conformation of the support elements 60 is possible through a description of one isolated support element, such as support element 60c. The support element 60c is coupled along the segment S3 to the interior surface 72 of the bag 58 and defines a height H and a thickness R. In some embodiments, the height H is less than the thickness R. The support element 60c is thinner, then, in height H than it is in thickness R. The relatively thinner height dimension H allows for compact collapse of the liner 28, and the generally thicker thickness R provides lateral stiffness and a resistance to lateral collapse of the support element 60c.

Regardless of the specific number, the support elements 60a, 60b, 60c, 60d when spaced as described above limit the lateral collapse of the bag 58 such that the bag 58 will not laterally collapse onto itself (e.g., the extent or amount of lateral collapse permitted by the support elements 60a-60d is equal to or less than width or diameter W of the bag 58). In particular, when the liner 28 is evacuated, the bag 58 collapses longitudinally and laterally, with the opposing faces 68, 70 collapsing inwardly toward one another in regions of the bag 58 apart from the support elements 60a-60d. It is desired to prevent the opposing faces 68, 70 from touching, as this could potentially occlude the flow of liquid along the longitudinal direction of the liner 28 and form pools of retained medical waste inside the liner 28. The support elements 60 are resistant to lateral collapse, and the segments S1-S4 of the bag 58 that are coupled to the support elements 60a-60d, respectively, are likewise restrained from laterally collapsing, such that the faces 68, 70 are restrained from contacting one another as the bag 58 collapses longitudinally.

In this manner, uncontrolled lateral collapse of the bag 58 is inhibited by the support elements 60 that prevent/restrain the opposing faces 68, 70 from touching one another. Thus, the support elements 60 are drawn longitudinally toward one another as the bag 58 collapses laterally and longitudinally, and the support elements 60 simultaneously impede the opposing faces 68, 70 of the bag 58 from touching. In other words, the liner 28 can be maximally collapsed longitudinally, with the support elements 60 ensuring that the bag 58 will not laterally collapse onto itself.

In some embodiments, a location of the support elements 60 relative to a length of the bag 58 correlates with a standardized volume, thus providing a user with the ability to quickly estimate the volume of liquid contained in the bag 58. For example, and with reference to the one embodiment of FIGS. 3 and 4, the fourth support element 60d can be located relative to a length of the bag 58 to be indicative of 1 liter of contained liquid; the third support element 60c indicative of 2 liters of contained liquid; etc. In other words, when the level of the contained liquid (with the liner 28 in the upright orientation of FIGS. 3 and 4) is approximately at or even with the fourth support element 60d, the user can visually ascertain or estimate that approximately 1 liter of liquid is contained in the liner 28; when the contained liquid level is approximately at or even with the third support element, the user can visually ascertain or estimate that approximately 2 liters of liquid is contained in the liner 28; etc. A wide variety of other volumetric values can be implicated by the support elements 60 (e.g., 0.5 liter, 1.0 liter, 1.5 liter, etc.; 0.25 gallon, 0.5 gallon; etc.). Along these same lines, the support elements 60 can be configured to provide a visual indication of the contained liquid volume represented by the corresponding support element 60 location. For example, the support elements 60 can be color coded to enhance a user's ability to visually distinguish the support elements 60 from one another, and thus the contained liquid volume represented by each support element 60 (e.g., each of the support elements 60a-60d can be of a different color, such as the fourth support element 60d, the third support element 60c being blue, etc.). Similarly, the support elements 60 can have written indicia (not shown) representative of the contained liquid volume associated therewith (e.g., the fourth support element 60d can include the written indicia "1 liter"; the third support element 60c can include the written indicia "2 liters"; etc.).

Figure 5:
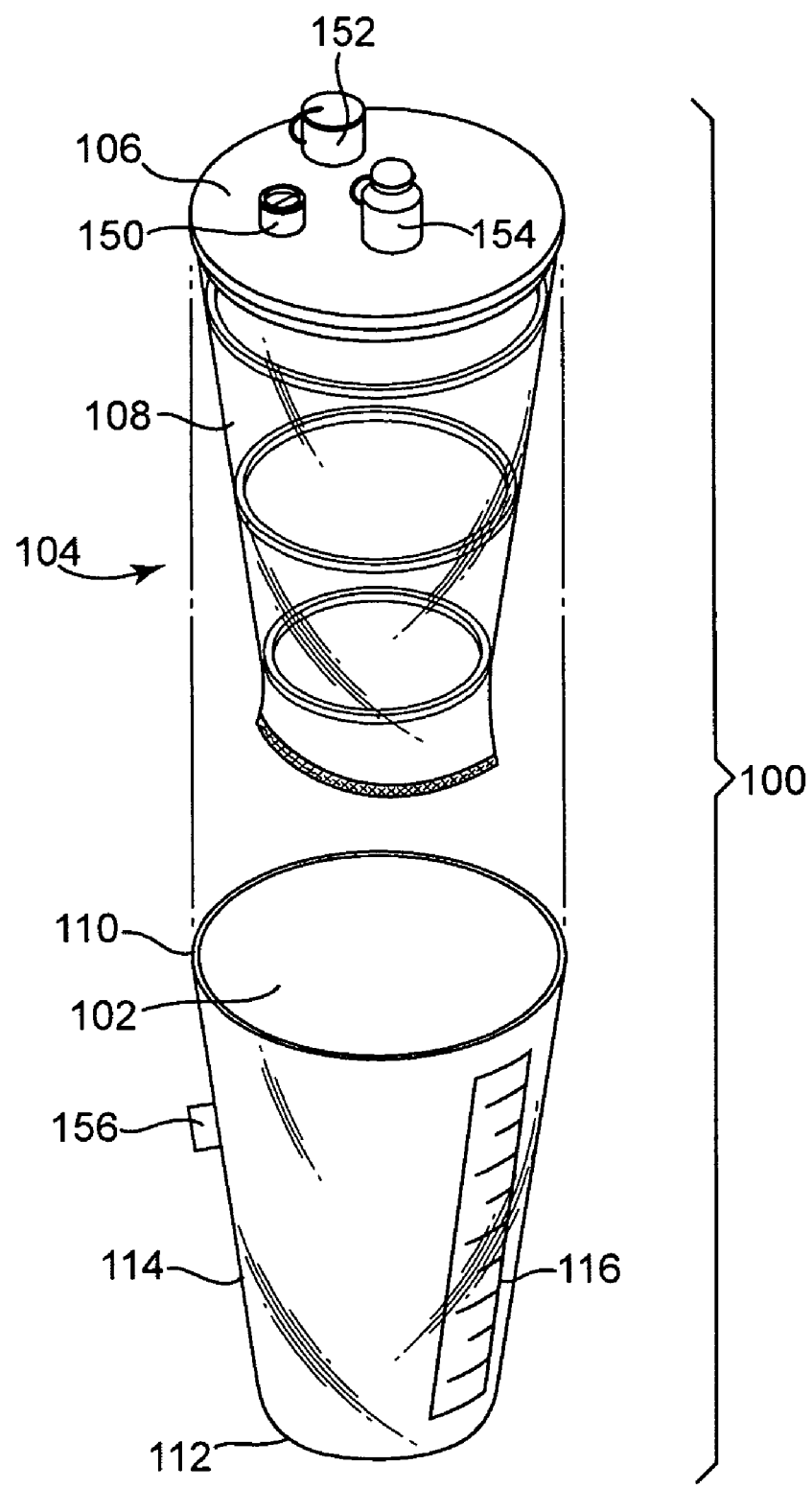
FIG. 5 illustrates components of another medical fluid collection system in accordance with principles of the present invention.

FIG. 5 illustrates components of another medical fluid collection system 100 according to principles of the present invention. The system 100 includes a canister 102 and a liner assembly 104 removably coupleable to the canister 102. The liner assembly 104 includes a lid 106 and a collapsible liner 108 coupled to the lid 106. In general, the lid 106 is sized to be attached and sealed to the canister 102, and the collapsible liner 108 is sized to be disposed within the canister 102. The collapsible liner 108 is a repository for the collection of medical waste fluids, and is configured to uniformly and completely collapse to discharge the medical waste fluids during a disposal process.

The canister 102 is generally a durable, impact resistant container that includes an open end 110, a base 112, and a wall 114 tapering between the open end 110 and the base 112. As illustrated, the open end 110 defines a generally circular cross-section, although it is to be understood that other shapes and sizes for the canister 102 are also acceptable. Generally, the canister 102 is reusable and suited for repeated use with single use, disposable liner assemblies 104. In one embodiment, the canister 102 is molded from high impact plastic, and includes a graduated scale 116 useful in measuring a collected volume of medical waste. Suitable rigid canisters 102 include canisters provided as a component of a Medi-Vac® Suction Canister System, available from Cardinal Heath of Dublin, Ohio.

The lid 106 is substantially similar to the lid 26 illustrated in FIG. 2. In this regard, the lid 106 can include one or more ports (e.g., ports 150-154). The canister 102 can similarly include a port 156 akin to the port 52 (FIG. 1) previously described).

Figure 6:
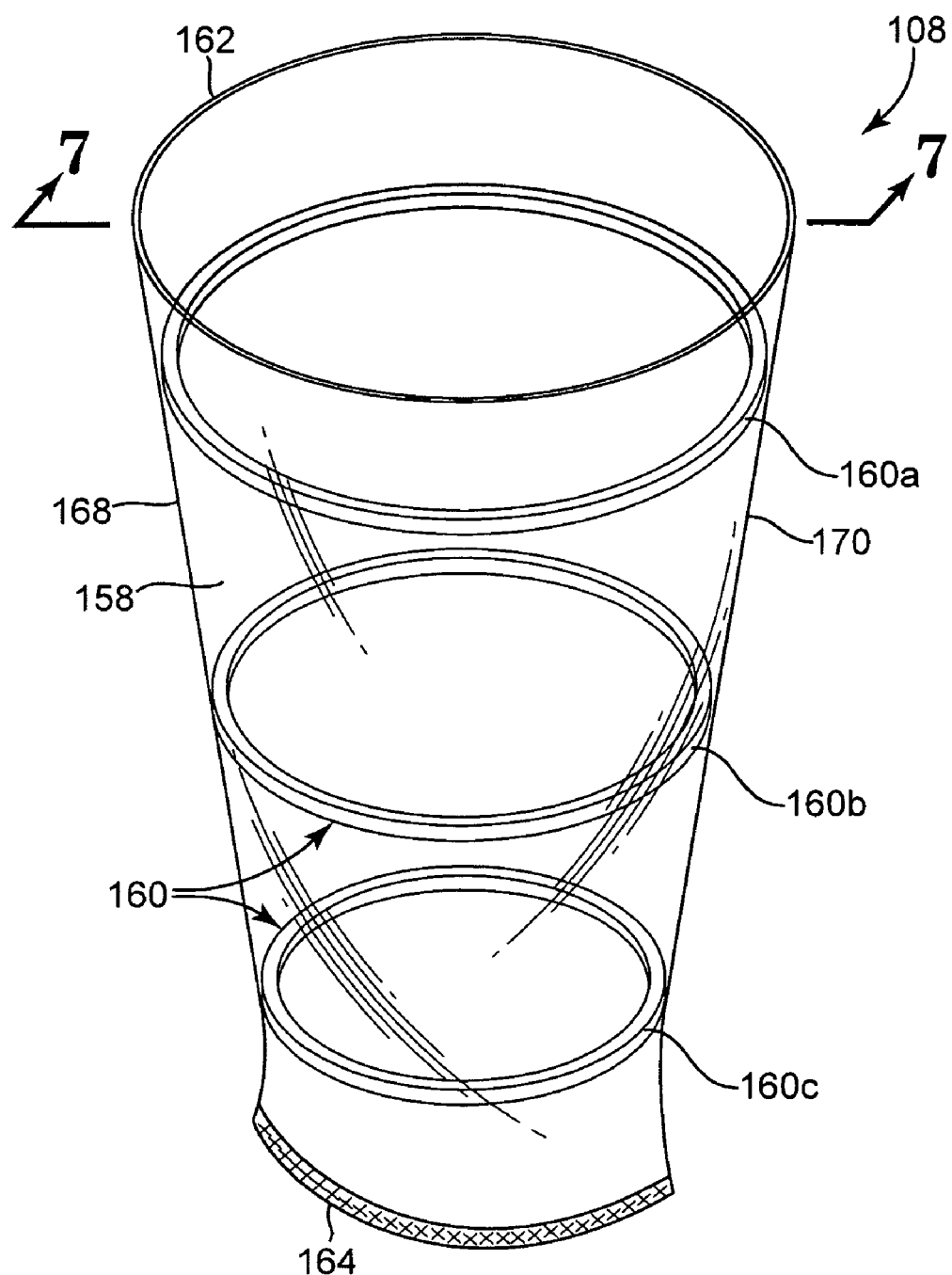
FIG. 6 is a perspective view of a collapsible liner component of the system of FIG. 5.
Figure 7:
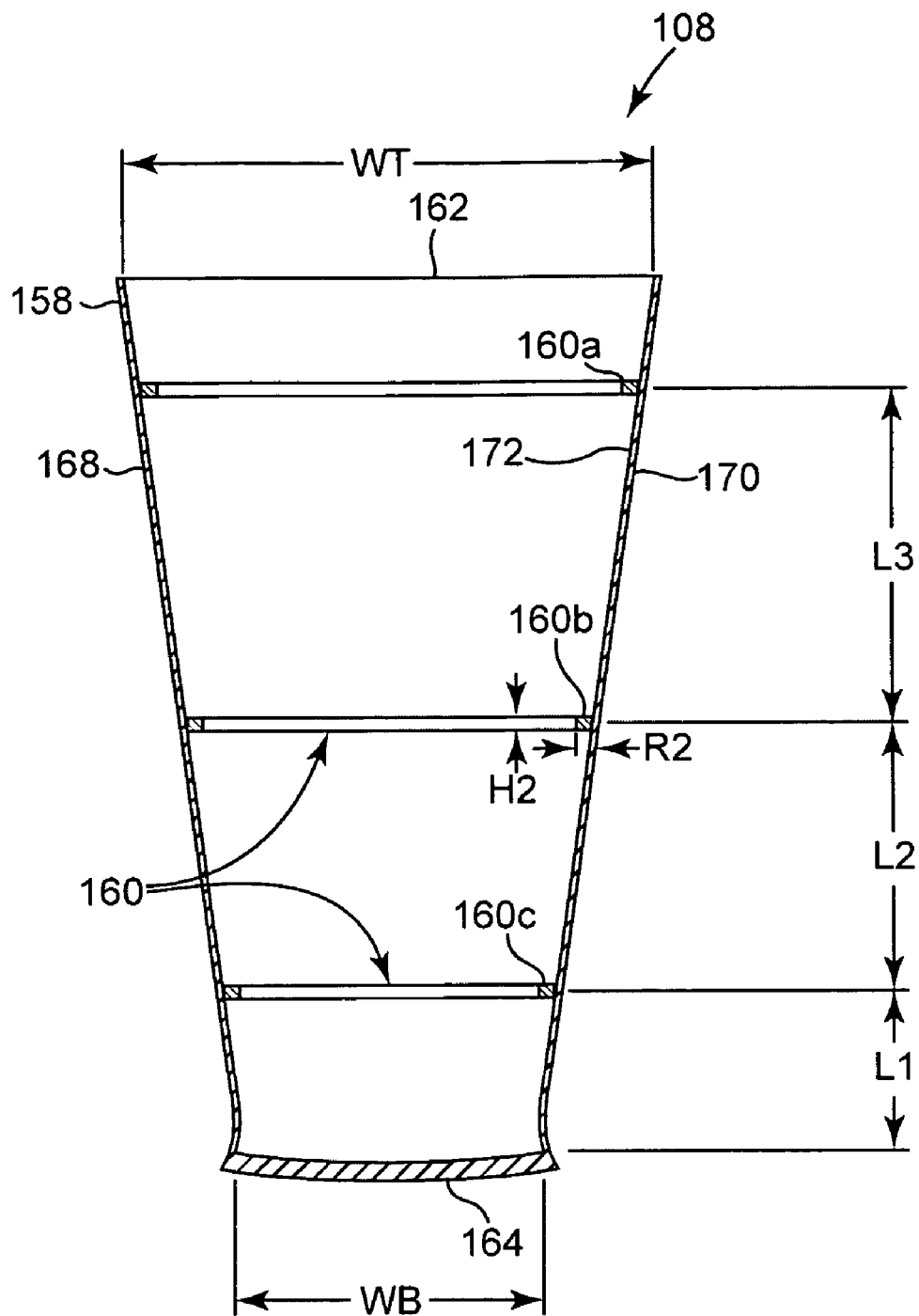
FIG. 7 is a cross-sectional view of the collapsible liner of FIG. 6.

FIG. 6 illustrates a perspective view and FIG. 7 illustrates a cross-sectional view of the collapsible liner 108 separate from the lid 106 in accordance with principles of the present invention. The collapsible liner 108 includes a bag 158 and one or more support elements 160 disposed substantially laterally relative to the bag 158. In this regard, the liner 108 is substantially similar in configuration to the liner 28 (FIG. 3), and various embodiments provide for the support elements 160 to be separately formed and attached to the bag 158, or alternatively, some embodiments provide for the bag 158 and the support elements 160 to be integrally formed.

In general, the bag 158 defines a top portion 162 opposite a closed bottom portion 164, and in one embodiment the bag 158 is tapered to extend longitudinally between the top portion 162 and the bottom portion 164 to define an interior within which medical waste fluid (not shown) can be contained. The top portion 162 is not sealed shut and is configured for attachment to, the lid 106 (FIG. 5) as previously described. The bottom portion 164 is generally sealed, or otherwise closed off, and prevents the passage of fluids through the bottom portion 164 of the bag 158.

The bag 158 is flexible, and comparatively, the support elements 160 are not. For example, in one embodiment the bag 158 is flexible enough to enable pressure in the range of about 0.1 to 1 ATM vacuum to collapse the bag 158, as described above with respect to the bag 58 (FIG. 3). In this regard, suitable materials for the bag 158 include polyolefins that are RF weldable to the support elements 160, such as ethylene methyl acrylate, although other polymers are also acceptable.

The support elements 160 (exemplary first-third support elements 166a, 166b, 166c are illustrated in FIG. 6) are provided to limit lateral collapse in a manner that is substantially similar to the support elements 60 described above. That is to say, support elements 160 allow the bag 158 to collapse both laterally and longitudinally in the presence of a vacuum at the bag's interior, but the lateral collapse is controlled to facilitate a maximum longitudinal collapse of the bag 158 from the bottom portion 164 up to the top portion 162 during evacuation of medical waste fluids. With this in mind, although three support elements 160a, 160b, 160c are illustrated, it is to be understood that one or more support elements 160 can be generally laterally disposed relative to the bag 158 to control lateral collapse of the liner 108.

The support elements 160 are, in general, disposed generally laterally between the top portion 162 and the bottom portion 164 of the bag 158. For example and with reference to FIG. 7, the bag 158 defines, in longitudinal cross-section, opposing faces 168, 170 that are separated by a lateral bag width. Since the bag 158 is tapered, the opposing faces 168, 170 taper between a generally wider dimension (e.g., diameter) at or adjacent the top portion 162 to a generally narrower dimension (e.g., diameter) at or adjacent the bottom portion 164. In this regard, the tapered bag 158 defines a first lateral bag width (e.g., diameter) WT extending between the opposing faces 168, 170 adjacent the top portion 162, and a second narrower lateral bag width (e.g., diameter) WB extending between the opposing faces 168, 170 adjacent the bottom portion 164. The support elements 160 are distributed longitudinally between the top portion 162 and the closed bottom portion 164, with the third support element 160c longitudinally spaced from the bottom portion 164 by a spacing distance L1, adjacent second and third support elements 160b and 160c longitudinally spaced by a spacing distance L2, and adjacent first and second support elements 160a and 160b longitudinally spaced by a spacing distance L3. Because the bag 158 is tapered, in some embodiments, L3 can be greater than L2, and L2 can be greater than L1, although in other embodiments the spacing distances L1-L3 are substantially identical.

In general, the respective spacing distances L1-L3 is not greater than the minimum lateral bag width or diameter in a corresponding region of the bag 158. For example, relative to region defined between the bottom portion 164 and the third support element 160c, the second lateral bag width WB represents the minimum lateral bag width in that region, with the spacing distance L1 thus being less than or equal to the minimum lateral bag width WB. With this longitudinal positioning, the third support element 160c will prevent the bag 158 from laterally collapsing on to itself (e.g., the opposing forces 168, 170 are prevented from contacting one another at a longitudinal center line of the bag 158) in the region between the bottom portion 164 and the third support element 160c.

Because the bag 158 is tapered (e.g., expanding in diameter from bottom to top), the minimum lateral bag width relative to the region between the third support element 160c and the second support element 160b is greater than that associated with the region between the bottom portion 164 and the third support element 160c, and instead approximates the lateral bag width or diameter defined by the third support element 160c. In this case, the spacing distance L2 is less than or equal to the lateral dimension (e.g., diameter or width) of the third support element 160c. In other words, due to the taper in the bag 158, L2 can be slightly greater than L1. A similar relationship can exist for the spacing distance L3 between the first and second support elements 160a, 160b; namely, the spacing distance L3 is less than or equal to the minimum bag width in the corresponding region, with this minimum width being defined by the second support element 160b. Thus, the spacing distance L3 is less than or equal to the transverse dimension (width or diameter) of the second support element 160b. That is to say, for the tapered bag 158, the adjacent second and third support elements 160b and 160c can be longitudinally closer together than the adjacent first and second support elements 160a and 160b.

As noted above, for low volume liners 108 having an overall length that is short relative to width, one support element 160 located between the top portion 162 and the closed bottom portion 164 can be sufficient to limit the lateral collapse of the liner 108 to an amount that is not greater than the bag width in the region of collapse.

In this manner, when the bag 158 collapses laterally, the opposing faces 168, 170 collapse inwardly toward one another in regions apart from the support element(s) 160. Simultaneously, adjacent ones of the support elements 160 are longitudinally drawn toward one another (e.g., as the bag 158 collapses, the third support element 160c is longitudinally drawn toward the second support element 160b). Thus, the bag 158 collapses longitudinally and laterally, but a lateral collapse within a given region is constrained such that the opposing faces 168, 170 do not contact one another. The support elements 160 thus inhibit lateral collapse of the bag 158 while permitting longitudinal collapse of the bag 158.

The support elements 160 are, in general, formed of a polyolefin, and are substantially similar in composition to the support elements 60 (FIG. 2) described above. For example, in one embodiment the support elements 160 are formed of ethylene methyl acrylate, although other suitable materials for forming the support elements 160 are also acceptable.

The support elements 160a-160c are illustrated in FIG. 7 as being connected to an interior surface 172 of the bag 158, although other embodiments provide for the support elements 160a-160c to be connected to an exterior surface of the bag 158. In general, the support elements 160a-160c have a similar configuration. The following description is related to the second support element 160b, although it is to be understood that the description applies equally to the first and third support elements 160a, 160c.

The second support element 160b defines a height H2 and a thickness R2. In one embodiment, the second support element 160b is thinner in height H2 than it is in thickness R2. The relatively thinner height dimension H2 allows for compact collapse of the liner 108, and the generally thicker thickness R2 provides lateral stiffness and a resistance to the lateral collapse of the second support element 160b.

Figure 8A:
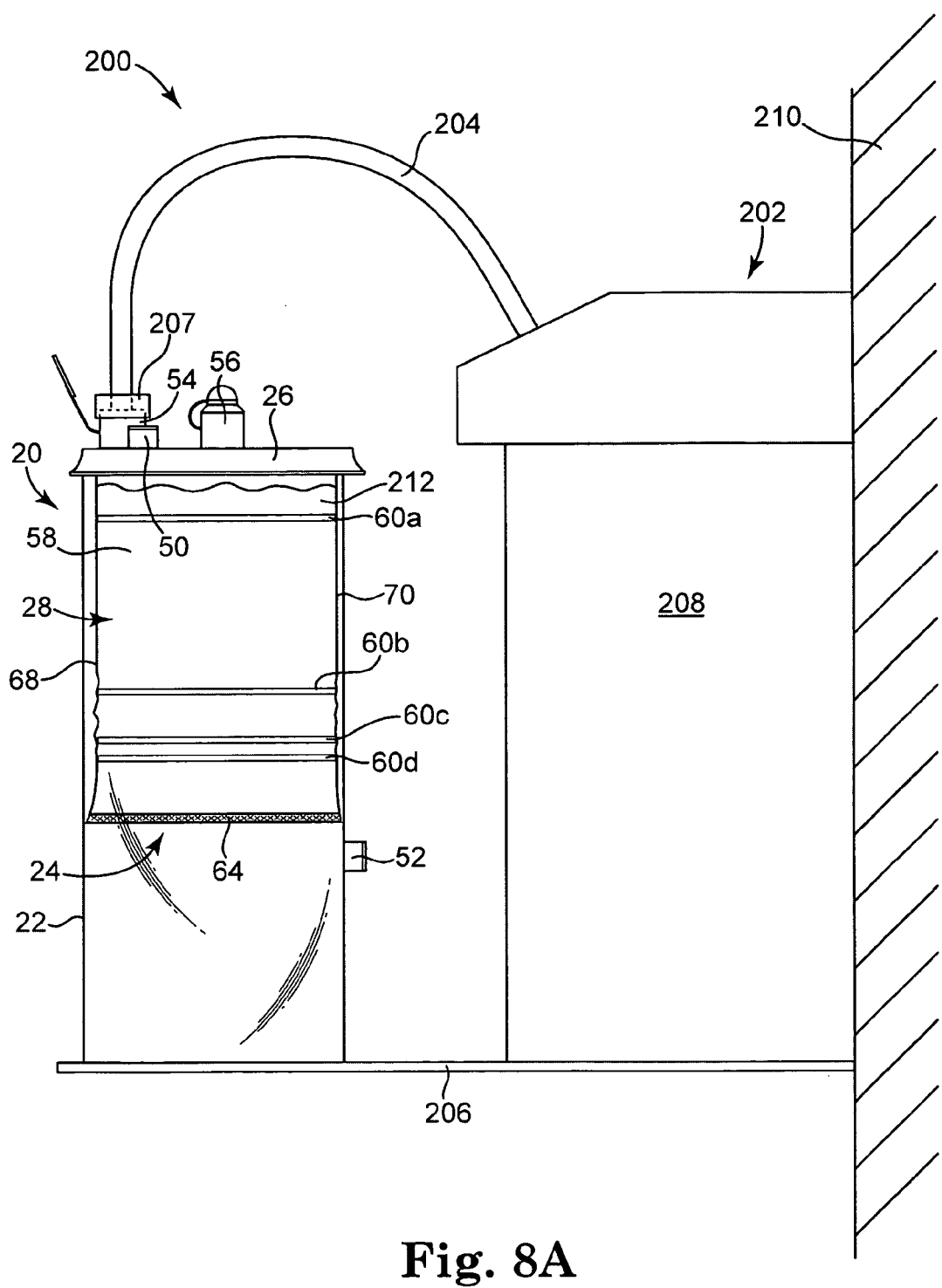
FIG. 8A is a side view of a medical fluid collection system operatively coupled to a medical waste disposal system in accordance with principles of the present invention.

FIG. 8A illustrates components of a medical waste disposal system 200 according to principles of the present invention. Waste disposal system 200 includes a suction pump system 202 including a suction line 204, and a platform 206 that is sized to retain the medical fluid collection system 20. In one embodiment, a housing 208 of the suction pump system 202 is mounted to a wall 210 that is provided with a water source and a drain (neither shown). The water source provides a flow of water, for example tap water, and the flowing water creates suction by the Bernoulli principle that enables the suction line 204 to suction contents from the collapsible liner 28 into the drain within the wall 210.

During waste disposal, medical waste fluid 212 contained within the collapsible liner 28 is pumped out of the liner 28 by the suction line 204, and the liner 28 is collapsed under the suction force of the suction pump system 202. In this regard, the medical waste fluid 212 is shown for illustrative purposes spaced slightly away from the lid 26, although it is to be understood that in actual practice the medical waste fluid 212 would be "at" the lid 26 as the fluid 212 is drawn into the discharge port 54.

In one example of medical waste disposal, the medical fluid collection system 20 is placed on the platform 206 and a connector 207 of the suction line 204 is connected to an opened discharge port 54 (as illustrated). In this regard, other ports that communicate with an interior of the liner 28, such as the patient tubing port 56 and the first vacuum source port 50,are closed to prevent bypass of the suction initiated by the suction pump system 202. During disposal of the medical waste fluid 212 from the liner 28, the second vacuum source port 52 (otherwise fluidly connected to the space between the canister 22 and the liner 28) is vented to atmosphere so that the space between the liner 28 and the canister 22 can fill with atmospheric air as the liner 28/bag 58 collapses.

The connector 207 is sealed or otherwise attached to the discharge port 54. The vacuum source of the suction pump system 202 is activated, and the suction through the suction line 204 evacuates the medical waste fluid 212 from the collapsible liner 28. Other vacuum sources suited for evacuating the liner 28 are also acceptable and within the scope of this application. In any regard, suction from the suction line 204 collapses the liner 28, which elevates the medical waste liquid 212 within the liner 28 toward the lid 26, enabling the suction liner 204 to expel the medical waste liquid 212 from the liner 28.

In particular, the suction through the suction line 204 causes the bag 58 to collapse laterally inward toward the center line of the liner 28. The support elements 60 are located to prevent contact of the opposing faces 68, 70 during longitudinal collapse of the liner 28. In other words, the support elements 60 limit the lateral collapse of the liner 28, and permit a longitudinal collapse of the liner 28 such that the bottom portion 64 is drawn towards the lid 26, thus expelling the medical waste fluid 212 out of the suction line 204. In this regard, the support element 60d has been longitudinally displaced toward the support element 60c such that the liner 28 is partially longitudinally collapsed. Additional subsequent suction through the suction line 204 will continue to evacuate the medical waste 212 and further longitudinally collapse the liner 28.

Figure 8B:
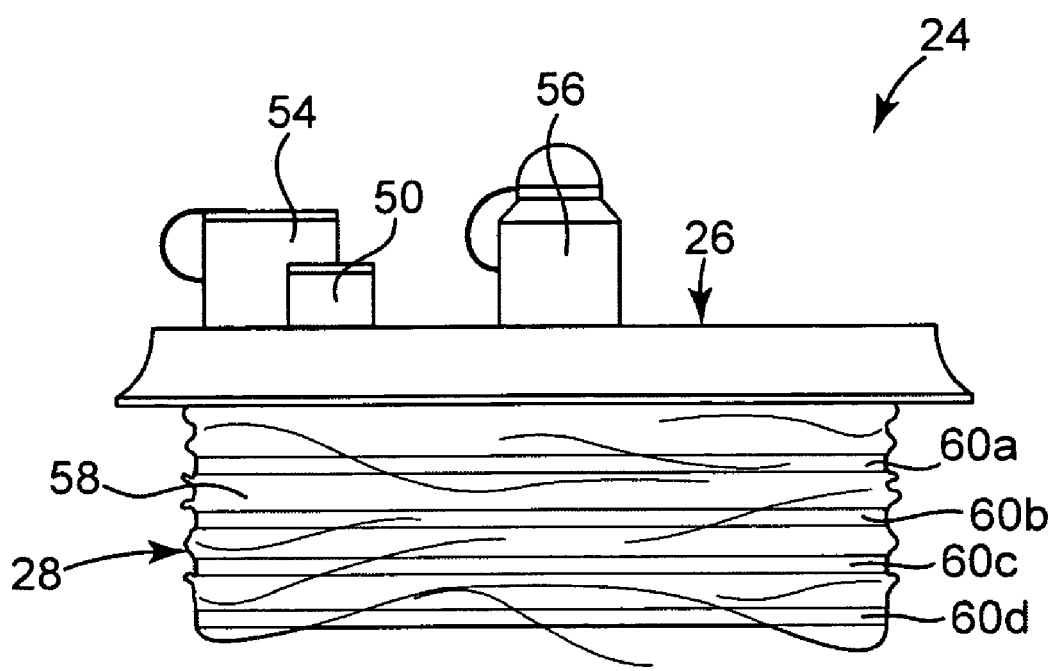
FIG. 8B illustrates a disposable liner assembly in a collapsed state according to principles of the present invention.

FIG. 8B illustrates the disposable liner assembly 24 in a collapsed state. The liner 28 has been longitudinally collapsed with the bottom portion 64 (FIG. 8A) drawn into the liner assembly 24 (and out of view), and substantially all of the medical waste fluid 212 (FIG. 8A) has been removed from the bag 58. In one embodiment, the liner assembly 24 is collapsed to a maximum extent such that the support element 60a is longitudinally displaced upward (relative to the orientation of FIG. 8B) and contacts the lid 26. However, for ease of illustration, the liner assembly 24 is shown in a collapsed state in which the support element 60a has been longitudinally displaced upward to a position adjacent to the lid 26.

With this in mind, and relative to FIG. 8B, the support element 60d has been displaced and longitudinally drawn up toward the support element 60c, and the support element 60c has been displaced and longitudinally drawn up toward the support element 60b, and the support element 60b has been displaced and longitudinally drawn up toward the support element 60a, and the support element 60a has been displaced and longitudinally drawn up toward the lid 26, with compacted segments of the bag 58 gathered in a central region of the liner 28 and gathered between support element 60a-66d.

In this manner, an internal volume of the liner 28 is minimized, which minimizes a volume of the liner assembly 24 that is ultimately disposed of.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of collapsible liner bags, liner assemblies, and/or medical fluid collection systems discussed herein. Therefore, it is intended that this invention be limited only by the claims and the equivalents thereof.

What is claimed is:

1. A medical fluid waste collection liner assembly for use with a medical fluid collection canister comprising:
   a lid configured to be removably attached to the canister, the lid including a vacuum port and a collection port; and
   a liner coupled to the lid, the liner including:
      a flexible film bag extending longitudinally between a top portion and a closed bottom portion and defining an interior, and
      at least one support element apart from the lid and connected to a segment of the bag;
   wherein the vacuum port and the collection port are in direct fluid communication with the interior of the bag,
   wherein when the interior of the bag is subjected to a vacuum during evacuation of fluid waste, the bag, except for the segment of the bag coupled to the at least one support element, laterally collapses so that the closed bottom portion and the at least one support element are displaced longitudinally toward the lid, and
   wherein the closed bottom portion is flexibly configured to longitudinally displace further into the interior when the at least one support element reaches a limit of longitudinal displacement toward the lid for removing substantially all of the fluid waste from the bag.

2. The liner assembly of claim 1, wherein the at least one support element is a rigid annular plastic band that defines a height and a thickness, the height being less than the thickness.

3. The liner assembly of claim 1, wherein the at least one support element is coupled to an interior surface of the bag between the top and bottom portions.

4. The liner assembly of claim 1, wherein a flexibility of the bag is greater than a flexibility of the at least one support element.

5. The liner assembly of claim 1, wherein the at least one support element is integrally formed as a portion of the flexible bag.

6. The liner assembly of claim 1, wherein the lid further includes a discharge port in direct fluid communication with the interior.

7. The liner assembly of claim 1, wherein the liner is attached to an outer circumferential surface of the lid.

8. The liner assembly of claim 1, wherein the liner includes a plurality of support elements discretely arranged along the bag between the top and bottom portions, each of the support elements being separated from an adjacent support element by a spacing distance.

9. The liner assembly of claim 8, wherein in longitudinal cross-section, the bag defines opposing faces separated by a lateral bag width, and further wherein the spacing distance between at least one pair of adjacent support elements is not greater than the lateral bag width.

10. The liner assembly of claim 8, wherein the plurality of support elements includes first and second support elements associated with the bag to define a bag region between the first and second support elements, and further wherein when the interior of the bag is subjected to a vacuum, the bag region experiences lateral and longitudinal collapse, with first and second support elements inhibiting an extent of the lateral collapse of the bag region.

11. The liner assembly of claim 8, wherein in longitudinal cross-section, the bag defines opposing faces that taper from a wide end adjacent to the top portion to a narrow end adjacent to the bottom portion, the faces between each pair of adjacent support elements defining a corresponding minimum bag width, and further wherein a spacing distance between adjacent support elements is not greater than the corresponding minimum bag width.

12. The liner assembly of claim 8, wherein the plurality of support elements includes a first support element positioned adjacent the bottom portion and a second support element positioned adjacent the first support element opposite the bottom portion, and further wherein longitudinal locations of the first and second support elements relative to the bag are indicative of standard volumes.

13. The liner assembly of claim 12, wherein the first support element is longitudinally located relative to the bag to reflect a filled volume between the first support element and the bottom portion of a first standard volumetric value, and the second support element is longitudinally located relative to the bag to reflect a filled volume between the second support element and the bottom portion of a second standard volumetric value, wherein the second standardized value is two times the first standardized value.

14. The liner assembly of claim 13, wherein the first standard volumetric value is 1 liter and the second standard volumetric value is 2 liters.

15. The liner assembly of claim 12, wherein a color of the first support element is different from a color of the second support element, the colors configured to provide a comparative visual indication of a filled volume.

16. A medical fluid collection system comprising:
a canister defining an open end; and
a liner assembly including:
   a lid removably attachable to the open end of the canister, the lid including a vacuum port and a collection port; and
   a collapsible liner dimensioned for placement within the canister, the liner including:
      a flexible film bag extending longitudinally between a top portion coupled to the lid and a closed bottom portion and defining an interior, and
      at least one support element apart from the lid and disposed generally laterally relative to the flexible bag;
wherein the vacuum port and the collection port are in direct fluid communication with the interior of the bag,
wherein when the interior of the bag is subjected to a vacuum during evacuation of fluid waste, except where constrained by the at least one support element, of the bag laterally collapses as the at least one support element and the closed bottom portion are displaced longitudinally toward the lid, and
wherein the closed bottom portion is flexibly configured to longitudinally displace further into the interior when the at least one support element reaches a limit of longitudinal displacement toward the lid for removing substantially all of the fluid waste from the bag.

17. The medical fluid collection system of claim 16, wherein the at least one support element is connected to a segment of the flexible bag such that the segment is not laterally collapsible when the interior of the bag is subjected to a vacuum.

18. The medical fluid collection system of claim 16, wherein the liner includes a plurality of support elements connected to the flexible bag in a discretely spaced fashion.

19. The medical fluid collection system of claim 18, wherein in longitudinal cross-section, the flexible bag defines opposing faces separated by a lateral bag width, and further wherein a longitudinal spacing distance between at least two adjacent support elements is not greater than the bag width.

20. The medical fluid collection system of claim 16, wherein the canister includes a second vacuum source port for subjecting a space between the collapsible liner and the canister to a second vacuum commensurate to the vacuum applied to the interior of the bag.

* * * * *